(12) United States Patent
Nakayama et al.

(10) Patent No.: US 10,088,450 B2
(45) Date of Patent: Oct. 2, 2018

(54) METHOD FOR EVALUATING STRUCTURAL CHANGE DURING PRODUCTION PROCESS, AND ANALYSIS PROGRAM

(71) Applicant: HITACHI, LTD., Tokyo (JP)

(72) Inventors: Takeshi Nakayama, Tokyo (JP); Masanari Koguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/526,231

(22) PCT Filed: Dec. 8, 2014

(86) PCT No.: PCT/JP2014/082423
§ 371 (c)(1),
(2) Date: May 11, 2017

(87) PCT Pub. No.: WO2016/092615
PCT Pub. Date: Jun. 16, 2016

(65) Prior Publication Data
US 2017/0315091 A1    Nov. 2, 2017

(51) Int. Cl.
*G01N 27/62* (2006.01)
*G01N 33/20* (2006.01)
*G01N 1/44* (2006.01)
*G01Q 10/00* (2010.01)
*H01J 37/285* (2006.01)

(52) U.S. Cl.
CPC .............. *G01N 27/62* (2013.01); *G01N 1/44* (2013.01); *G01N 33/20* (2013.01); *G01Q 10/00* (2013.01); *H01J 37/285* (2013.01)

(58) Field of Classification Search
CPC .......... G01N 27/62; G01N 1/44; G01N 33/20; G01Q 10/00; H01J 37/285
See application file for complete search history.

(56) References Cited

U.S. PATENT DOCUMENTS

| 2003/0190132 A1* | 10/2003 | Gadkaree | ................ | C30B 33/00 385/129 |
| 2011/0134424 A1* | 6/2011 | Park | ........................ | G01N 21/73 356/316 |
| 2013/0213945 A1* | 8/2013 | Stegmann | ............... | G01N 1/286 219/121.83 |

FOREIGN PATENT DOCUMENTS

JP    H08-114612 A    5/1996

OTHER PUBLICATIONS

T. Kinno, et al., Laser-assisted atom probe tomography of 18O-enriched oxide thin film for quantitative analysis of oxygen, Applied Surface Science. 290 (2014) 194-198.
O. Moutanabbir, et al., Ultraviolet-laser atom-probe tomographic three-dimensional atom-by-atom mapping of isotopically modulated Si nanoscopic layers, Applied Physics Letters, Jan. 7, 2011, vol. 98, p. 013111-1-013111-3.
(Continued)

*Primary Examiner* — Wyatt Stoffa
*Assistant Examiner* — Sean Luck
(74) *Attorney, Agent, or Firm* — Volpe and Koenig, P.C.

(57) ABSTRACT

Areas having different isotopic ratios are artificially introduced into a metal material before sintering, a heat treatment, or grain boundary diffusion, and atom probe analysis results before and after sintering, a heat treatment, or grain boundary diffusion are compared to evaluate a change in isotopic distribution over time.

6 Claims, 8 Drawing Sheets

(56) References Cited

OTHER PUBLICATIONS

M. Thuvander et al., APFIM Studies of Grain and Phase Boundaries: A Review, Materials Characterization, Jan. 2000, vol. 44, No. 1-2, pp. 87-100.
J. Takahashi, et. al., Progress of three-dimensional atom probe techniques for analysis of steel materials:development of atom probe specimen preparation techniques for site-specific regions, Shinnittetsu Giho, 2010, No. 390 20-27.
International Search Report for WO 2016/092615 A1, dated Mar. 10, 2015.

* cited by examiner

METHOD FOR EVALUATING STRUCTURAL CHANGE DURING PRODUCTION PROCESS, AND ANALYSIS PROGRAM

TECHNICAL FIELD

The present invention relates to a method for evaluating a structural change during a production process of a powder metallurgy material produced according to sintering, a heat treatment, or grain boundary diffusion, and an analysis program executing the evaluation.

BACKGROUND ART

One of construction methods for producing a shaped raw material is a method referred to as powder metallurgy. In the powder metallurgy, metal powders as starting materials are mainly bonded to each other according to a sintering phenomenon, to produce a material. The powder metallurgy is used for shaped raw material production in a wide range of areas such as a magnetic material, an ultrahard alloy, a mechanical structure application part, atomic fuel, and ceramics. Examples of the feature of the powder metallurgy include the following items (1) and (2): (1) an alloy composition can be freely controlled by merely changing the combination or the blending ratio of starting material powders; and (2) the powder metallurgy has a simple step of heating a molded body having a shape almost close to an end product shape to provide an excellent material yield ratio and less consumption energy.

The physical properties of a material obtained by powder metallurgy are largely influenced by the fine structure formation or the composition of the material. In recent years, a small amount (1% or less) of an addition element, a micro structure of 0.1 μm or less, or arrangement of an atomic level, or the like frequently influences the physical properties of the material largely. The production method of the target material or the control method of the material physical properties becomes important. To that end, it is important to understand a change in a structure occurring in the material at any stage during sintering and a heat treatment. Particularly, from the understanding of the movement of an atom through a liquid phase in liquid phase sintering or the like, the optimal process can be considered in order to obtain the target material physical properties or achieve the target fine structure.

One of methods for observing the fine structure is an atom probe. The atom probe can directly observe atomic arrangement or composition distribution of a leading end of a material which has been processed so as to be needle-shaped, at an atomic scale. In the atom probe, a high direct current voltage is applied so as to cause the leading end of the needle-shaped material to generate a high electric field. A pulse voltage is applied or a pulse laser is irradiated to the leading end so that field evaporation of an atom belonging to a first layer of a surface is induced. Then, the mass of an ion which has field-evaporated is time-of-flight-measured so that a type of an element can be determined. The field evaporation progresses every atomic layer. For this reason, atom probe analysis has resolution in a depth direction at an atomic level.

Since the atom probe is time-of-flight type analysis, the kind of the element is recognized by a ratio of mass to valence (=mass charge ratio). For this reason, a system in which an element A and an element B having a mass number of constant multiple (about 2 or 3 times) thereof are mixed makes it difficult to perform quantitive identification of both the elements. For example, the analysis of silicon (Si) having a mass number of 28 contained in iron (Fe) having a mass number of 56, or the analysis of carbon (C) having a mass number of 12 contained in magnesium (Mg) having a mass number of 24, or the like is difficult.

On the other hand, the atom probe analysis can distinguish the same elements (isotope) having different mass numbers. Therefore, if an isotope of nitrogen having a mass number of 15 is introduced into a material in order to analyze nitrogen (N) having a mass number 14 contained in silicon (Si) having a mass number of 28, the weak point of the atom probe analysis can be overcome (NPL 1). Incidentally, in elemental analysis according to fluorescence or Auger electrons such as EDX (energy dispersion type X-ray analysis), the same elements having different mass numbers cannot be distinguished.

CITATION LIST

Non-Patent Literature

NPL 1: Appl. Surf. Sci. 290 (2014) 194

SUMMARY OF INVENTION

Technical Problem

An analysis technique using an isotope as a marker is used in various fields. For example, an organic chemical field uses a technique of detecting or pursuing the nuclear spin of a stable isotope such as $^{13}C$ contained in a compound obtained as a result of a chemical reaction according to NMR (nuclear magnetic resonance) measurement. An earth science field investigates the ratio of a stable isotope according to mass analysis to measure the date. A technique of diffusing a radioactive isotope in a metal to estimate a diffusion length from the intensity of radiation according to each region is also used.

However, at present, a method for purposely removing an isotopic ratio from a natural isotopic ratio for a practical metal material, and subjecting the difference between the isotopic ratios to atom probe analysis to investigate the history of local element diffusion is not performed. The isotope of a specific element has the same electronic state, which hardly causes a chemical difference in reactivity in a material, or the like even if the isotopic ratio is changed. Therefore, a test piece can be made using a process of producing a real material. No difference in fundamental characteristics between the test piece and a normal product exists, and the composition of the test piece is equal to that of the normal product.

Therefore, the test piece is temporarily caught up in an actual product, which causes no problem and also makes it impossible to distinguish the test piece from composition analysis such as EDX (energy dispersion type X-ray analysis) or Auger electron spectroscopy.

A precise sintered body is obtained by a heat treatment referred to as sintering in the production of powder metallurgy or ceramics. However, the production step of a material according to a heat treatment process is extremely complicated, which makes it difficult to design appropriate dependence on any heat treatment process or production process in order to realize the target fine structure. As one cause, it is considered that the movement of an atom at a micrometer or nanometer order cannot be directly observed during a heat treatment process. It is important for process analysis aiming at an improvement in material property to clarify the movement of an atom according to solid phase diffusion or liquid phase diffusion during a heat treatment. Particularly, the presence of an element X over a plurality of phases makes it very difficult to pursue the movement of the element X.

Then, the present inventors provide a method for evaluating a structural change during a production process of a powder metallurgy material which could not be recognized heretofore according to the thermal diffusion of the same element kind, or the like, and an analysis program Solution to Problem In order to solve the problems, a typical embodiment of the invention is "a method for artificially introducing areas having different isotopic ratios into a metal material before sintering, a heat treatment, or grain boundary diffusion, and comparing atom probe analysis results before and after sintering, a heat treatment, or grain boundary diffusion to evaluate a change in isotopic distribution over time".

Another typical embodiment of the invention is "an analysis program causing a computer to execute: a first step of receiving inputting of one or more known isotopic ratios R1 to Rm by a user, wherein the one or more known isotopic ratios R1 to Rm are different from that of a material purposely mixed with a metal material; a second step of calculating an isotopic ratio Ri0 for each of minute volume areas Ei from a mass charge ratio spectrum measured for a sample cut from the metal material; a third step of searching an isotopic ratio Ri coinciding with the isotopic ratio Ri0 with predetermined accuracy among a known natural isotopic ratio Rnat and the isotopic ratios R1 to Rm; and a fourth step of displaying an elemental map expressing the minute volume areas Ei with a visually distinguishable color and/or shape corresponding to the isotopic ratio Ri.

Advantageous Effects of Invention

According to one embodiment of the invention, the thermal diffusion of an element X generated from a specific phase in each heat treatment process of a powder metallurgy material can be three-dimensionally evaluated. Other problems, configurations, and advantages will become apparent from the following description of embodiments.

DESCRIPTION OF EMBODIMENTS

Hereinafter, embodiments of the preset invention will be described with reference to the accompanying drawings.

The embodiments of the present invention are not limited to embodiment examples described below, and a variety of modifications is possible within the spirit and scope of the present invention.

Example 1

In the present Example, in a material produced by a liquid phase sintering process in powder metallurgy, an evaluation method for clarifying a liquid phase area and a solid phase area during a heat treatment from the analysis of a solid metal sample at normal temperature will be described. The material property of the metal material here is known to strongly depend on the microstructure or nanostructure formation of the material. The structure formation is mostly generated by the diffusion of an element. Hereinafter, a method for investigating the diffusion history of an atom during a high-temperature heat treatment during a production process will be shown in order to improve the property of the metal material.

Figure 1:
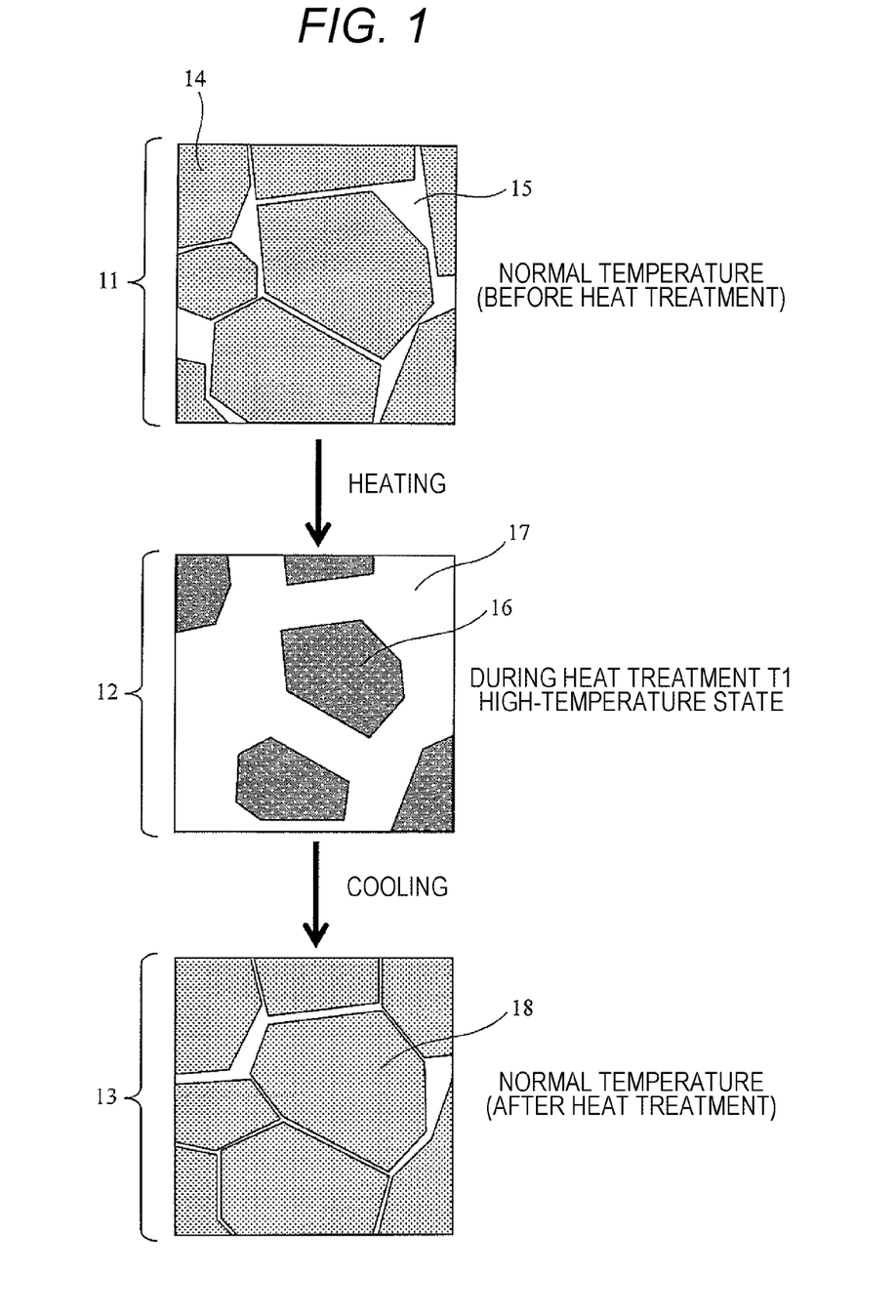
FIG. 1 conceptually illustrates a change in a material structure in a normal sintering process.

FIG. 1 shows a chancre in a metal structure in a heat treatment process in the production process of a metal material A. For example, the metal material A is produced by subjecting a material before heat treatment 11 to heat treatment T1 at a melting point or lower for a given length of time. An intergranular phase 15 has a lower melting point than that of a crystal grain 14. For this reason, the original intergranular phase 15 becomes a liquid phase 17 during the heat treatment T1. An element originally contained in the crystal grain 14 is also present in the liquid phase 17, and the crystal grain 14 which is sufficiently small in the material before heat treatment 11 mostly becomes the liquid phase 17 during the heat treatment T1. The element is mainly diffused in the liquid phase 17 during the heat treatment T1, and element diffusion in a solid phase 16 is smaller than the amount of diffusion in the liquid phase 17.

In a cooling process to normal temperature from a high-temperature state, the solid phase 16 takes the element from the liquid phase 17, and grows. The element taken in the solid phase 16 at this time maintains an element ratio so as to become equal to the crystal structure and the composition of the solid phase 16 serving as a core, which makes it impossible to clarify the presence position of a solid-liquid interface in a high-temperature state according to a composition analysis technique such as EDX (energy dispersion type X-ray analysis) with respect to a heat-treated crystal grain 18. If the position and the form of the solid-liquid interface during the heat treatment can be known, guidelines such as addition/non-addition of any element and any change/unchange in a heat treatment condition can be provided in the next material development. As a result, development for an improvement in the material property can be accelerated.

Figure 2:
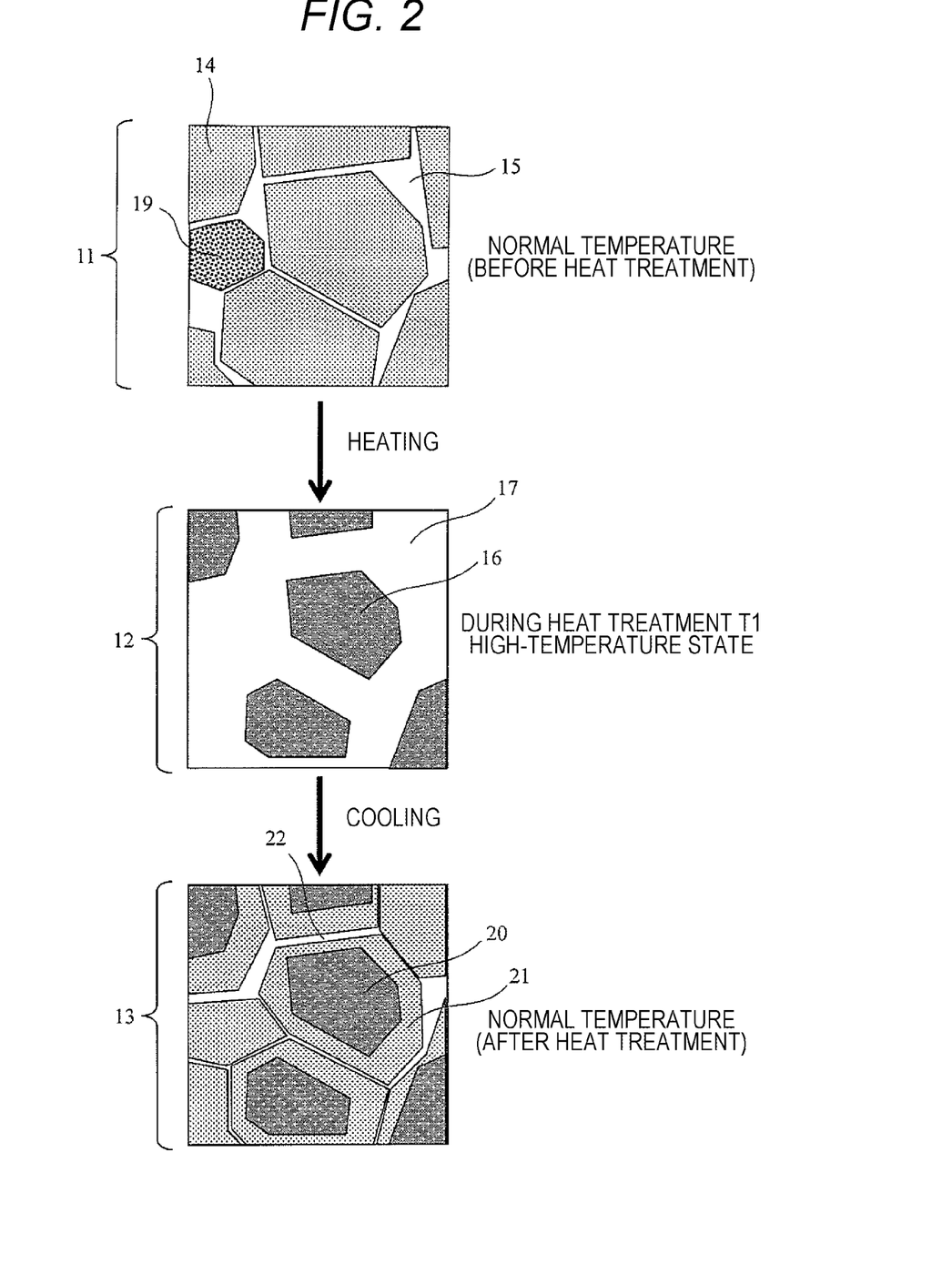
FIG. 2 conceptually illustrates a change in a material structure in a sintering process of Example 1.

Hereinafter, the solid-liquid interface of the metal material A in the high-temperature state is clarified using FIG. 2. FIG. 2 shows a structural change in the heat treatment process when a portion 19 having the same composition as that of the crystal grain 14 and an isotopic ratio different from that of the crystal grain 14 is purposely contained in the material before heat treatment 11 in the production process of the metal material A shown in FIG. 1. The isotopes of the same element have different nuclear structures, but the isotopes have the same electronic state, which provide the equivalent chemical nature. The metal material produced by the flow shown in FIG. 2 exhibits material property almost equivalent to that produced in FIG. 1. That is, a test piece exhibiting property completely equivalent to that of a real material can be obtained by a production process completely equivalent to that of the real material. Therefore, a material after heat treatment 13 in FIG. 2 exhibits property almost equivalent to that of the material after heat treatment 13 in FIG. 1.

As shown in FIG. 2, in the material after heat treatment 13, an isotopic ratio in an area 21 which is the liquid phase 17 in a high-temperature state is different from that in an area 20 which is the solid phase 16 also in a high-temperature state. However, the chemical compositions of the two areas 20 and 21 are equivalent. For this reason, the boundary surface of the two areas 20 and 21 cannot be distinguished by a spectroscopic method according to electron transition such as reflective electronic contrast of an electron microscope, EDX, or XAFS, but the boundary surface of the two areas 20 and 21 can be distinguished by an atom probe analysis method.

The boundary between the area 21 which is the liquid phase 17 in a high-temperature state and the area 20 which is the solid phase 16 in a high-temperature state in the material after heat treatment 13 is present near a grain boundary 22 between two crystals or at a position separated by a certain distance from the grain boundary 22 between two crystals in many cases. For this reason, the material after heat treatment 13 processed such that the interface is contained in a tip, to produce a needle sample for atom probes. The produced needle sample is subjected to atom probe analysis, and thereby the position of the solid-liquid interface of a real material in a high-temperature state can be confirmed.

Figure 3:
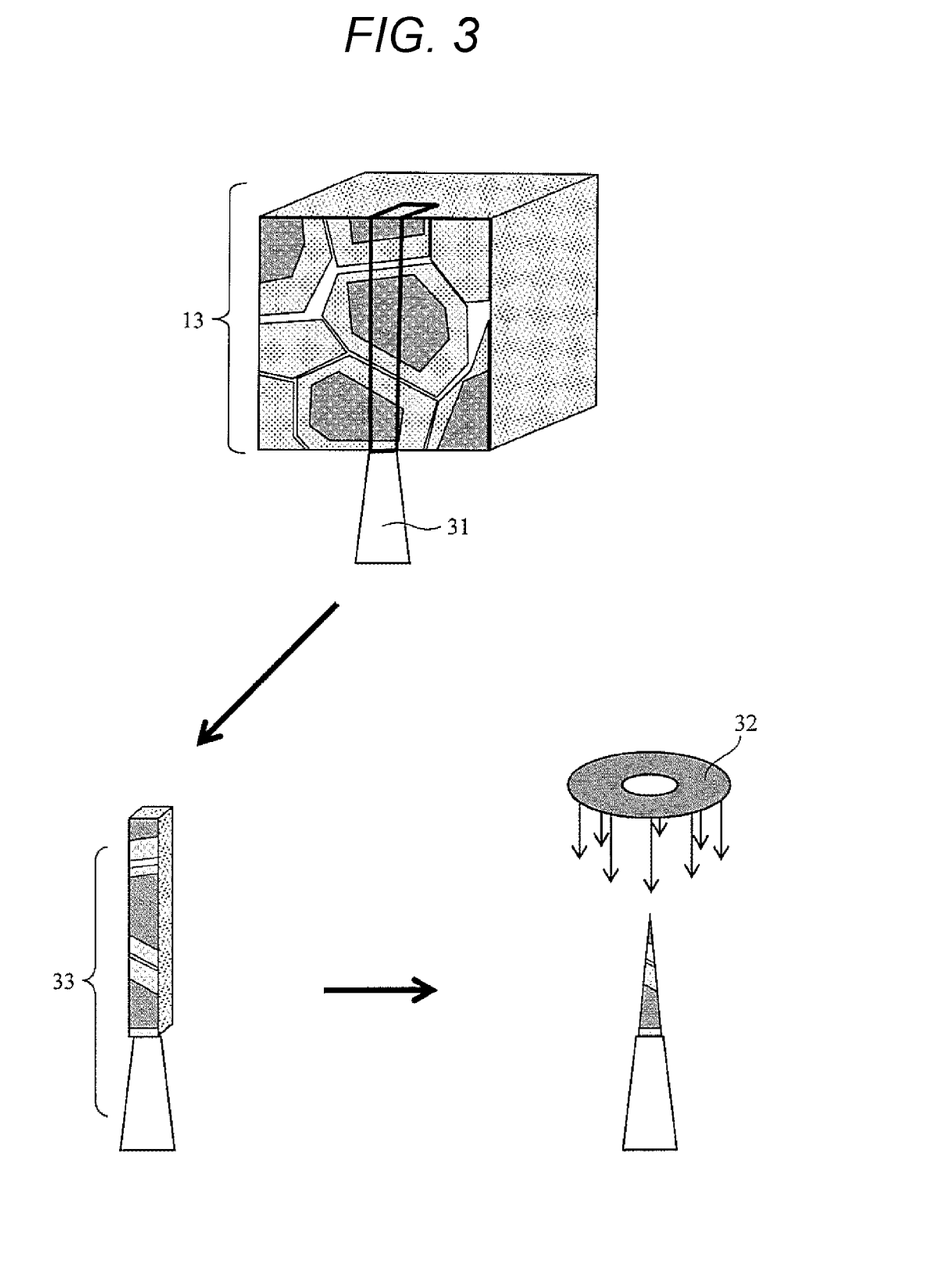
FIG. 3 illustrates a schematic production step of a needle sample for atom probes.

FIG. 3 illustrates a schematic step of producing a needle sample for atom probes from the material after heat treatment 13. FIB-SEM (focused ion beam-scanning electron microscope complex device) is mainly used for the production of the needle sample. First, one end of a small piece of the material after heat treatment 13 is fixed on a shaft 31. Next, a portion which is not required for the needle sample in the material after heat treatment 13 is cut by FIB, to produce a square column-like crudely processed needle sample 33. In this stage, the material placed on the shaft 31 has one side of hundreds nanometers to several millimeters. Then, the crudely processed needle sample 33 is subjected to FIB processing using an annular pattern 32 from above to complete a needle shape which can be subjected to atom probe analysis. The center of the annular pattern 32 is disposed on the axis line of the needle sample which is a final form. When the annular pattern 32 is used, an irradiation ion beam during the FIB processing does not hit the central part of the annular pattern 32. For this reason, the ion beam annularly cuts the crudely processed needle sample 33 from the outside thereof. Thereby, a needle-shaped sample (needle sample) having a sharpened tip is produced.

Figure 4:
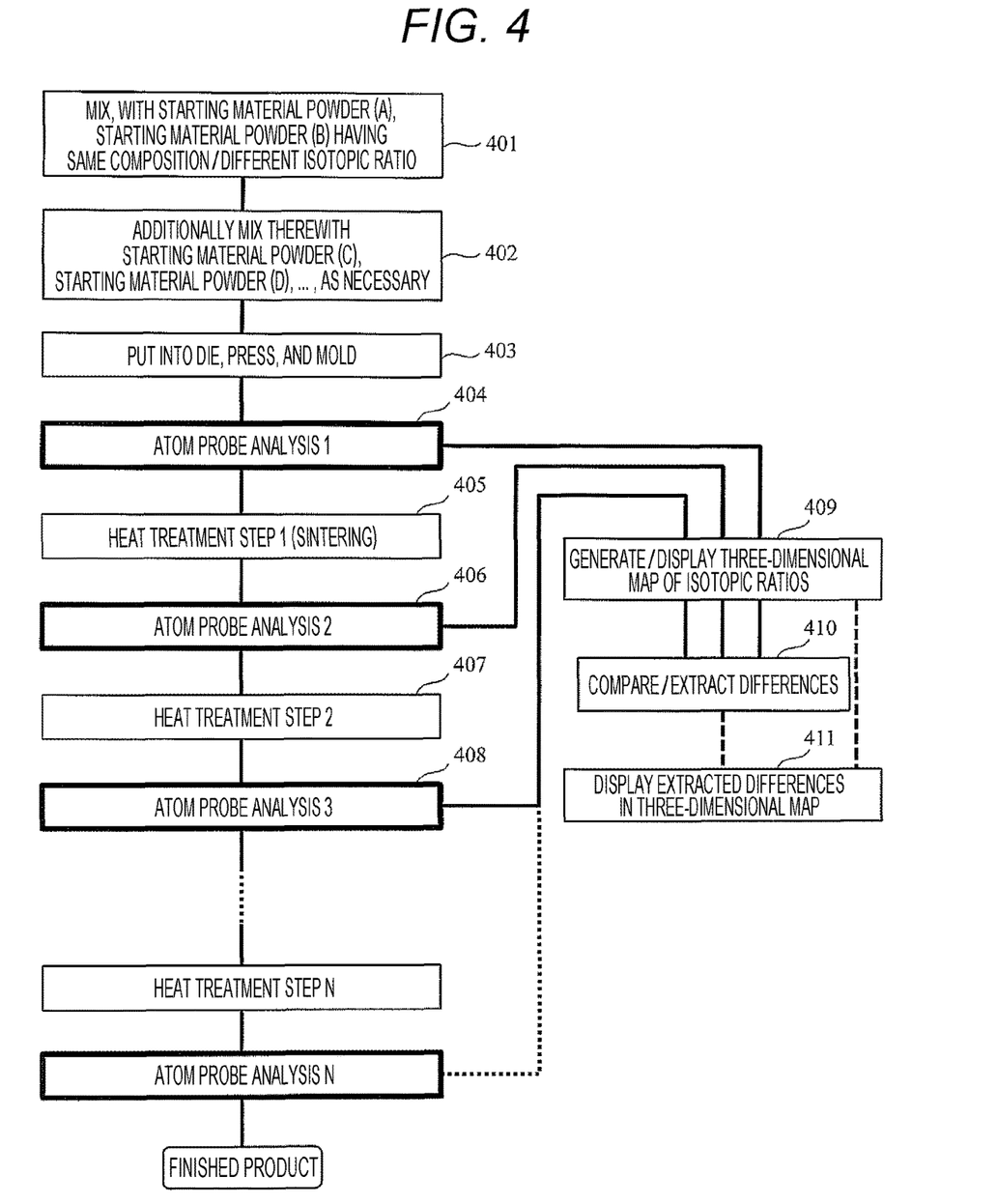
FIG. 4 is a flow chart describing an atom probe analysis step with an isotopic ratio as a probe.

FIG. 4 shows the whole atom probe analysis step according to the present Example.

Step 401

First, starting material powders A and B are mixed. The starting material powder B has the same composition as that of the starting material powder A, and the isotopic ratio of an element X contained in the starting material powder B is different from that in the starting material powder A. The starting material powder B is mixed at a constant rate with the starting material powder A. An isotopic ratio RA of the starting material powder A and an isotopic ratio RB of the starting material powder B are preferably different from each other as far as possible. The starting material powders may be mixed by worker's manual labor or automatically mixed using a mixing machine.

Step 402

Other starting material powder is additionally mixed with the mixed powder of the starting material powders A and B as necessary. The metal powder to be added may be one or more powders having an isotopic ratio different from those in the starting material powders A and B.

Step 403

The mixed powder put into a die is molded by a pressing machine. The molded body obtained at this time is obtained by merely mixing the starting material powders mechanically and packing the mixture. For this reason, the structure formation of the molded body is divided into areas clearly showing the isotopic ratio RA and the isotopic ratio RB for the element X as with the material before heat treatment 11 of FIG. 2. However, the contrasts of the areas cannot be confirmed by an analysis technique using an electron energy level width such as EDX or ABS.

Step 404

When the molded body is obtained, first atom probe analysis is executed. It is enough to cut a small piece of several nanometers to tens millimeters from the material for the atom probe analysis. For this reason, when a material having a millorder size which can mostly ignore a cutting size is analyzed, the analyzed material can be made to proceed to the next heat treatment step (sintering) as it is. Here, a needle sample for atom probes is produced by FIB-SEM as described above. The composition formation of the produced needle sample for atom probes is analyzed in an atom probe analyzing device.

Step 405

The molded body is subjected to a heat treatment step (sintering) after the small piece is cut. Specifically, a heat treatment is executed at a temperature lower than the melting point of the starting material powder constituting the molded body. The molded body is changed to a dense object (sintered body) by sintering.

Step 406

A small piece of several nanometers to tens millimeters is cut from the sintered body again, and a needle sample for atom probes produced for the small piece is subjected to atom probe analysis.

Step 407

The sintered body is subjected to a heat treatment step. In the heat treatment step, a heat treatment is executed at a temperature higher than the melting point of the starting material powder constituting the sintered body. According to the heat treatment step, as shown in FIG. 2, the material powders A and B are melted.

Step 408

A small piece of several nanometers to tens millimeters is cut from the material after the heat treatment step, and the needle sample for atom probes produced for the small piece is subjected to atom probe analysis. Even after this, each heat treatment step required for the production of an end product and atom probe analysis before and after the heat treatment step are executed.

Step 409

Data obtained by each atom probe analysis are collected by a calculator. The calculator generates and displays the three-dimensional map of the isotopic ratio of each sample based on the collected data. The step will be described in detail later.

Step 410

The calculator compares the three-dimensional maps obtained before and after the sintering and/or the heat treatment according to necessity for a user, and extracts the differences.

Step 411

The calculator displays the extracted differences in the three-dimensional map. By observing the three-dimensional map obtained in the step 409 or 410, the user can presume element movement during the heat treatment step.

Figure 5:
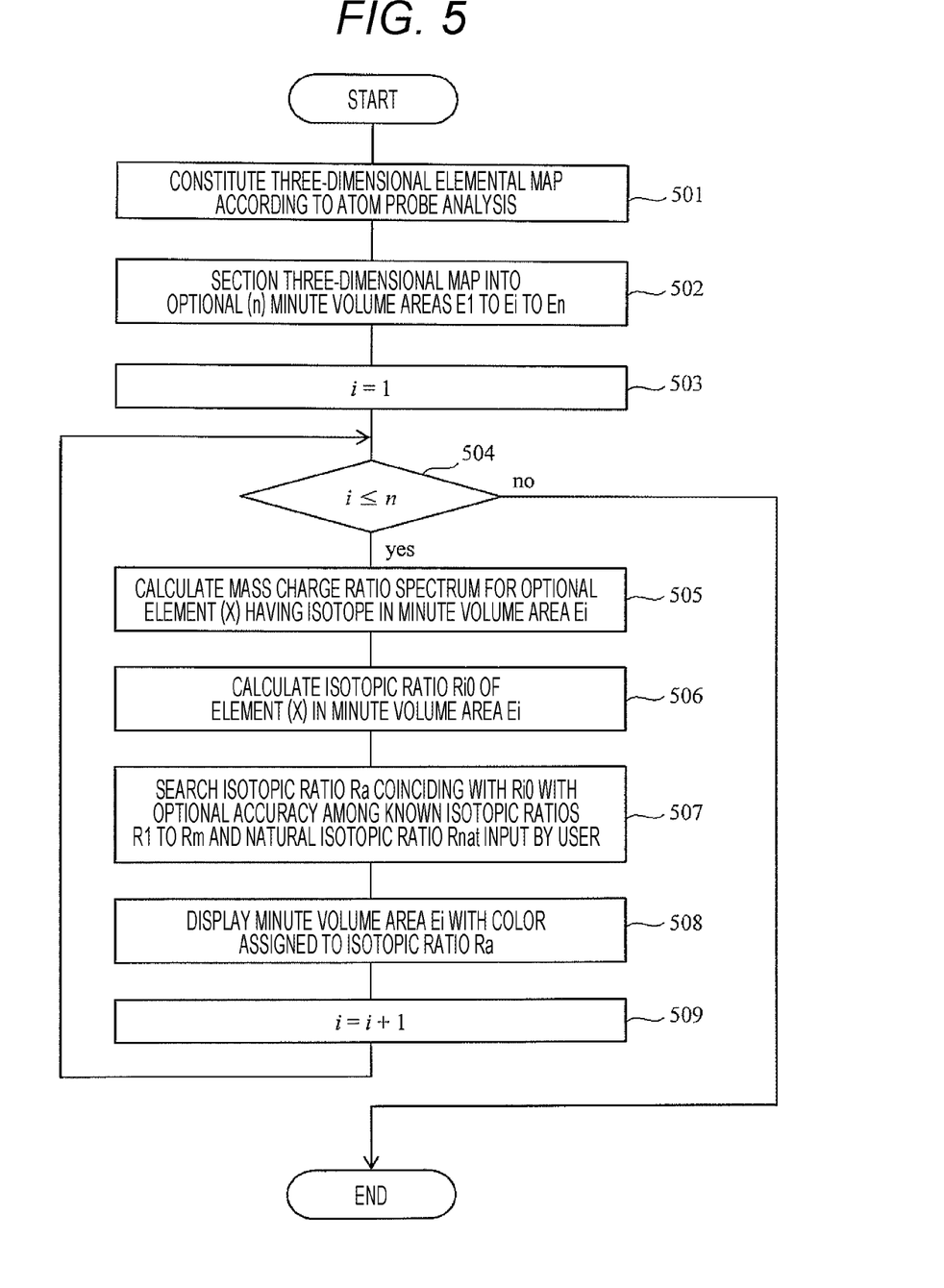
FIG. 5 is a flow chart of a step of obtaining isotopic ratio distribution from the results of atom probe analysis.

FIG. 5 shows processing contents executed in a step of treating the data obtained by the atom probe analysis (step of obtaining isotopic ratio distribution (three-dimensional map) from the analysis results).

Step 501

First, the calculator (computer) constitutes the three-dimensional elemental map of the sample in each stage during a production process based on the data obtained by the atom probe analysis. The constitution technique itself of three-dimensional elemental map is known.

Step 502

Next, by an optional minute volume area specified by the user (analysis person), the three-dimensional map is divided into n minute areas. As the volume of the minute area is decreased, analysis spatial resolution can be improved, but a calculation time increases, which causes deterioration in the analysis accuracy of the minute area to be described below. For this reason, generally, the deposition of the minute area is stopped in a size of about 1 to about 10 nm$^3$.

Step 503

The calculator sets a parameter i specifying a minute area to be analyzed as 1.

Step 504

The calculator determines whether the parameter i is equal to or less than n. The calculator proceeds to a step 505 when the parameter i is equal to or less than n, and ends the processing when the parameter i is more than n.

Step 505

The calculator calculates a mass charge ratio spectrum for an optional element X having an isotope in a minute volume area Ei specified by the parameter i.

Step 506

The calculator counts the number of atoms for every isotope of the element X from the calculated mass charge ratio spectrum, and divides the counted number of atoms by the total count number of the element X, to calculate an isotopic ratio Ri0 of the element X.

Step 507

The calculator compares the isotopic ratio Ri0 obtained in the step 506 with known isotopic ratios R1 to Rm and a natural isotopic ratio Rnat input by the user (analysis person) or obtained by calculating, and searches an isotopic ratio Ra coinciding with the isotopic ratio Ri0 with optional accuracy. Thereby, the isotopic ratio Pa of the minute volume area Ei is determined. Here, the calculator reads the known isotopic ratios R1 to Rm from the natural isotopic ratio database of the element, for example.

Step 508

The calculator expresses the minute volume area Ei on the three-dimensional map with a visually distinguishable color and/or shape assigned to the isotopic ratio Ra.

Step 509

The calculator adds 1 to the parameter i, and returns to the step 504. If the parameter i is more than n, a series of processings are ended. As described above, the isotopic ratio in the area 21 (FIG. 2) which is the liquid phase 17 (FIG. 2) in the high-temperature state is different from that in the area 20 (FIG. 2) which is the solid phase 16 (FIG. 2) in the high-temperature state. For this reason, the portion 20 and the portion 21 are expressed by the minute volume areas Ei expressed with different colors or shapes. In the three-dimensional map, the user (analysis person) can immediately recognize the three-dimensional distribution of the isotopic ratio in the sample visually. The user (analysis person) can quantitatively confirm the presence of the boundary surface between the portion 20 and the portion 21 in any region separated from the grain boundary 22 between two crystals (FIG. 2).

Figure 6:
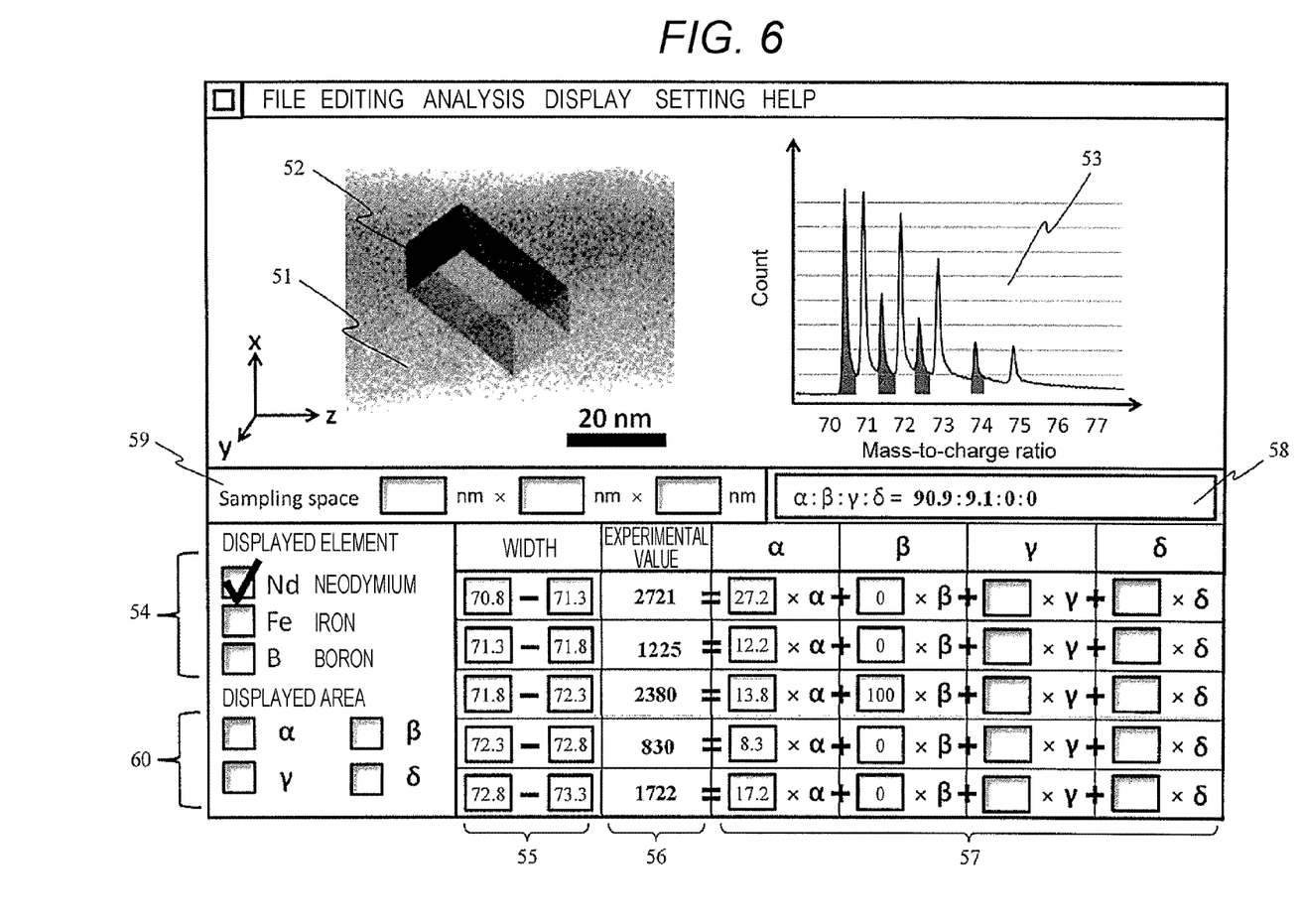
FIG. 6 shows an example of a user interface of an analysis program.

FIG. 6 shows an example of a user interface screen displayed on an operation screen by an analysis program executed by the calculator (calculator). FIG. 6 shows an example when an analysis program according to Example is used for the atom probe analysis of a neodymium magnet material. The three-dimensional elemental map (three-dimensional reconstructed image 51) constituted from the results of the atom probe analysis is displayed on the upper left of the screen.

A display element selection column 54 is displayed on the lower left of the screen. The element displayed on the screen can be selected by selecting a check box provided in display element selection column 54. By selecting of a plurality of check boxes, a plurality of elements can also be simultaneously displayed with different colors. The color displayed on the screen for every element can be freely changed by the user (analysis person)'s specification. Iron (Fe), neodymium (Nd), and boron (B) are mainly contained in a neodymium magnet, and in FIG. 6, only a neodymium (Nd) element is mapping-displayed. The isotope of the neodymium (Nd) element is selection-displayed in a display area selection column 60.

A mass charge ratio spectrum 53 of an element contained in an analyzed area (that is, minute volume area) 52 is displayed on the upper right of the screen. The analyzed area 52 is an area specified from the three-dimensional reconstructed image 51 by the user (analysis person). The size and the position of the analyzed area 52 can be freely deformed and moved by the user (analysis person). For example, the size of the analyzed area 52 can be optionally applied by the user (analysis person) through a volume input window 59 provided on the left side in the middle of the screen. Isotopes having mass numbers "142", "143", "144", "145", "146", "148", and "150" mainly exist in a neodymium element. For this reason, in the example of FIG. 6, seven peaks of a Nd element becoming a divalent positive ion can be confirmed between "71" and "75" in an abscissa axis in the mass charge ratio spectrum 53.

A peak width specification column 55, a number of atoms column 56, and a known isotopic ratio input column 57 are disposed on the lower side of the screen. If the user (analysis person) specifies, one by one, widths in which the peak of the isotope appears through the peak width specification column 55, the analysis program counts the number of atoms from the mass charge ratio spectrum 53 for every specified peak width, and automatically displays the counted number of atoms in the number of atoms column 56.

Each of the isotopic ratios of a material (a phase) having a Nd natural isotopic ratio originally contained in the material, and a material β, γ, and θ phases) having an isotopic ratio purposely mixed by the user (analysis person) and diffused is automatically input by the analysis program, in each of blanks corresponding to α, β, γ, and θ phases in the known isotopic ratio input column 57. For example, the Nd natural isotopic ratios (a phase) are "27.2, 12.2, 13.8, 8.3, 17.2, 5.7, 5.6" in order from the smallest peak width (in FIG. 6, only five peak widths are displayed from the smallest peak width). The Nd isotopic ratios (β phase) mixed purposely by the user (analysis person) and diffused are "0, 0, 100, 0, 0, 0, 0" in order from the smallest peak width (in FIG. 6, only five peaks are displayed from the smallest where peak).

Here, the value of the number of atoms column 56 as the experimental result has the linear combination relationship between the value and the known isotopic ratios R1 to Rm (here, m=2) input in the known isotopic ratio input column 57. Based on the relationship, the analysis program automatically calculates a mixing ratio 58 (isotopic ratio Ri0) of the Nd atom derived from the α phase and the Nd atom derived from the β phase included in the analyzed area 52, and displays the mixing ratio 58 in a mixing ratio column 48.

Furthermore, the analysis program searches an isotopic ratio Ri coinciding with the mixing ratio 58 (isotopic ratio Ri0) obtained as a result of the above-mentioned calculation with predetermined accuracy from a known natural isotopic ratio Rnat and the known isotopic ratios R1 to Rm input by the user (analysis person). The analysis program maps a visually distinguishable color and/or shape corresponding to the searched isotopic ratio Ri in each analyzed area 52 of the three-dimensional reconstructed image 51. For example, the visually distinguishable color corresponding to the isotopic ratio Ri is expressed with a color according to the concentration ratio (isotopic ratio) of the Nd atom derived from the α phase and the Nd atom derived from the β phase. Thereby, the user (observer) can distinguishably observe a solid phase area in a high-temperature state and a liquid phase area in a high-temperature state, and can visually recognize the boundary surface of the areas from the contrast of the displayed color and/or shape.

Figure 7:
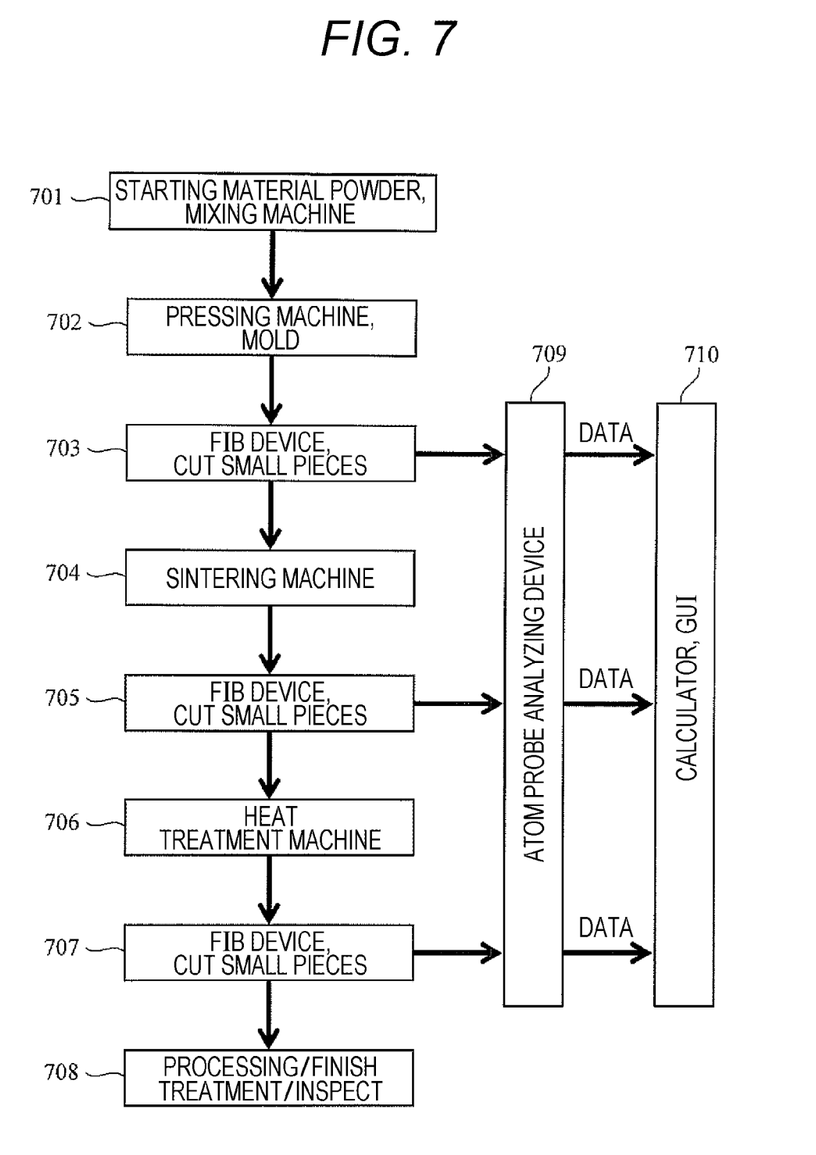
FIG. 7 illustrates the flow of data corresponding to a material in each working step.

FIG. 7 shows a data flow corresponding to a material in each working step.

Step 701

In the initial stage of the production process of powder metallurgy, starting material powders are mixed at a predetermined ratio using a mixing machine. The mixing machine mix the starting material powders such that the mixing ratio becomes uniform.

Step 702

The starting material powders after mixing are compression-molded by a pressing machine having a high-precision die. Thereby, a molded body is obtained.

Step 703

A small piece having a side of several nanometers to tens of millimeters is cut according to FIB processing from the molded body using a FIB device, and processed to a needle shape. A needle sample for atom probes produced by the FIB processing is set in an atom probe analyzing device 709 where the needle sample for atom probes is subjected to atom probe analysis. The results (data) of the atom probe analysis are applied to a calculator 710 from the atom probe analyzing device 709. The calculator 710 subjects the data to the above-mentioned processing. The small piece to be cut can also be used for observation using an electron microscope or the like as necessary.

Step 704

A sintering machine sinters the molded body after extracting the small piece, to produce sintered body.

Step 705

A small piece having a side of several nanometers to tens of millimeters is cut again by the FIB processing from the sintered body using the FIB device, and processed to a needle shape. A needle sample for atom probes produced by the FIB processing is set in an atom probe analyzing device 709 where the needle sample for atom probes is subjected to atom probe analysis. In this stage, the calculator 710 can acquire the atom probe analysis results before and after sintering. The calculator 710 compares element information on the sample obtained by the acquired atom probe analysis before sintering (including the elemental map described above) with element information on the sample obtained by atom probe analysis after sintering (including the elemental map described above), and calculates a change in isotopic distribution over time. For example, the movement amount and the diffusion original area of the purposely mixed metal material are calculated.

Step 706

The molded body after the small piece is cut is heat-treated at a temperature equal to or higher than a melting point using a heat treatment machine.

Step 707

A small piece having a side of several nanometers to tens of millimeters is cut again by the FIB processing from the molded body using the FIB device, and processed to a needle shape. A needle sample for atom probes produced by the FIB processing is set in an atom probe analyzing device 709 where the needle sample for atom probes is subjected to atom probe analysis. In this stage, the calculator 710 can acquire the atom probe analysis results before and after the heat treatment. The calculator 710 compares element information on the sample obtained by atom probe analysis before the heat treatment (including the elemental map described above) with element information on the sample obtained by atom probe analysis after the heat treatment (including the elemental map described above), and calculates a change in isotopic distribution over time.

Step 708

A processing treatment, a finish treatment, and an inspection treatment other than the heat treatment are executed using a device corresponding to each of the treatments.

According to the present Example, the thermal diffusion of the element X from a specific phase occurring according to each heat treatment step of a powder metallurgy material can be evaluated even if the same element is contained in another phase in the material. Thereby, the movement of the element in each heat treatment (also including sintering) can be three-dimensionally evaluated at an atom scale. Even if an area containing the same element is present in addition to the optional analyzed area in the sample after diffusion, the diffusion original area of a specific element can be identified by using the presence ratio of the diffusion original isotope as a probe.

Example 2

In the present Example, a process for clarifying a factor influencing the difficulty of local diffusion in the material such as a diffusion length and a direction difference of a diffusion element in a grain boundary diffusion treatment will be described. The diffusion aspect of the element in the material largely varies according to the kind or the diffusion path form of the element. Heretofore, the diffusion of the element has been investigated by a tracer diffusion method using a radioactive isotope and other analysis method such as SIMS.

However, as with the powder metallurgy, in the case of the distribution of diffusion in a real material in a fine structure having no reproducibility, particularly when the diffusion element is an element contained in a material in which the element is to be diffused, or when the element is contained in a plurality of phases in a material in which the element is to be diffused, it is difficult to follow the diffusion path. The present example uses the isotopic ratio of the diffusion element as a probe without using the diffusion element itself as the probe, and exhibits an effect in such a case.

Figure 8:
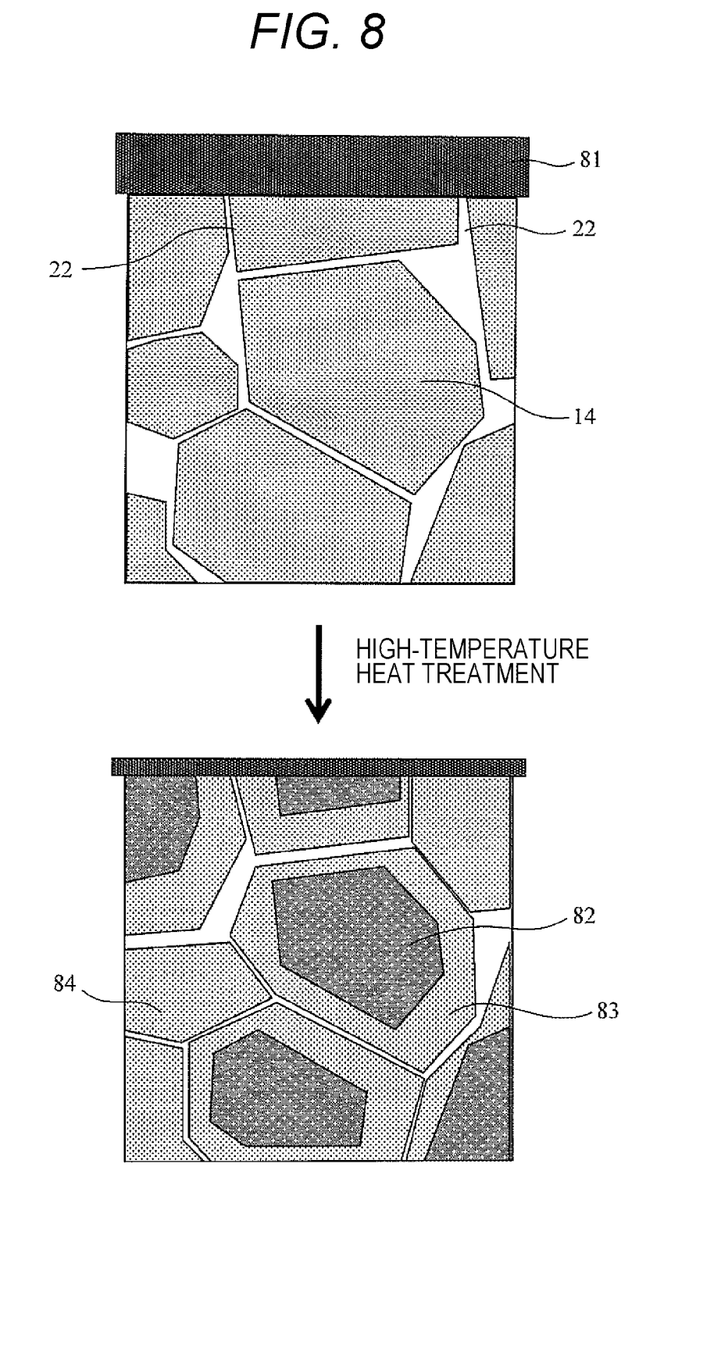
FIG. 8 conceptually illustrates a change in a material structure in a heat treatment process of Example 2.

FIG. 8 schematically shows a change occurring in a metal structure according to a high-temperature heat treatment in a state where a diffusion pair 41 containing an element Y is brought into contact with a metal material A. An element Y contained in the diffusion pair 41 is diffused through the grain boundary 22 between two crystals, and get across the whole material at a sufficient heat treatment temperature for a sufficient time. In the high-temperature state, the grain boundary between two crystals becomes a liquid phase, and the outer portion of each crystal grain is also considered to become a liquid phase to some extent.

Since the diffusion of the element Y in the liquid phase is more than that in the solid phase, the element Y is not observed at the vicinity 82 of the center of a large crystal grain in a finite-time heat treatment, but often observed on the outside 83 of the large crystal grain and in a small crystal grain 84.

The element Y is originally contained in the metal material, which makes it difficult to quantitatively pursue the element Y according to EDX or the like. However, if the element Y is pursued by atom probe analysis using the isotopic ratio as a probe, the path and the extent of the diffusion can be easily estimated.

The present Example is different from Example 1, and liquid phase diffusion is diffusion only from one direction at a macro scale. For this reason, the grain boundary diffusion length (micron) of the element Y can be investigated, and the three-dimensional direction of the crystal axis of the crystal grain can be investigated by the combination with EBSD (electron beam back-scattering diffractometry). For example, the occurrence of the liquid phase diffusion, or the like can be investigated according to the positional relationship between the orientation direction of the crystal grain and the grain boundary between two crystals.

Other Examples

The present invention is not limited to the above-mentioned Examples, and includes a variety of variations. For example, although the above-mentioned Examples have been described in detail to clearly illustrate the present invention, the present invention need not include all of the configurations described in the Examples. It is also possible to, for a part of a configuration of each Example, add, remove, or substitute a part of a known technique. Some or all of the above-mentioned configurations, functions, processing units, and processing means or the like may also be implemented as hardware by designing integrated circuits, for example.

The above-mentioned analysis program can be stored in a storage device such as memory, a hard disk, or a SSD (Solid State Drive); or a storage medium such as an IC card, an SD card, or a DVD. The control lines and information lines represent those which are considered to be necessary for the description, and represent not all control lines and information lines which are necessary for a product. In practice, almost all configurations may be considered to be mutually connected.

REFERENCE SIGNS LIST

11 material before heat treatment
12 material during heat treatment
13 material after heat treatment
14 crystal grain
15 intergranular phase
16 solid phase
17 liquid phase
18 crystal grain after sintering
19 portions having same composition and different isotopic ratios
20 solid phase area in high-temperature state
21 liquid phase area in high-temperature state
22 grain boundary between two crystals
31 shaft
32 annular processing pattern
51 three-dimensional reconstructed image
52 analyzed area
53 mass charge ratio spectrum in analyzed area
54 display element selection column
55 peak width specification column
56 number of atoms column
57 known isotopic ratio input column
58 mixing ratio column
59 volume input window
60 display area selection column
81 diffusion pair
82 vicinity of center of large crystal grain
83 outside of large crystal grain
84 small crystal grain

The invention claimed is:

1. A method for evaluating a structural change in a metal material during a production process,
the metal material produced by using a metal powder A containing an element X having a plurality of isotopes as a starting material according to a powder metallurgy method,
the method comprising:
a first step of mixing a metal powder A having an isotopic ratio RA with a metal powder B having an isotopic ratio RB and containing the same element X to obtain a mixed powder;
a second step of putting the mixed powder into a die, and pressing the mixed powder to obtain a molded material;
a third step of cutting a needle-shaped sample from the material that is not yet subject to a heat treatment or sintering, and subjecting the sample to atom probe analysis;
a fourth step of heat-treating or sintering the material that is not yet subject to a heat treatment or sintering;
a fifth step of cutting a needle-shaped sample from the material after the heat treatment or sintering, and subjecting the sample to atom probe analysis; and
a sixth step of comparing element information obtained by subjecting the material before a heat treatment or sintering to atom probe analysis with element information obtained by subjecting the material after a heat treatment or sintering to atom probe analysis, and measuring a change in isotopic distribution over time.

2. The method according to claim 1, further comprising a seventh step of heat-treating the material after the fifth step, and an eighth step of cutting a needle-shaped sample from the material after the seventh step, and subjecting the sample to atom probe analysis.

3. The method according to claim 1, wherein the sixth step includes a step of transforming a relationship between a coordinate in which an element constituting the metal material is present and an element kind corresponding to the coordinate into an elemental map.

4. The method according to claim 3, further comprising a seventh step of receiving a setting of minute volume areas dividing the elemental map, an eighth step of dividing the elemental map into the minute volume areas, a ninth step of counting the total number of atoms of the element X and the number of isotopic atoms of the element X for each of the minute volume areas, a tenth step of obtaining an isotopic ratio Ri for each of the minute volume areas, and a 11th step of displaying isotopic distribution of the element X with the isotopic ratio Ri.

5. The method according to claim 1, wherein the first step adds one or more kinds of metal powders containing the element X having an isotopic ratio different from those of the metal powder A and the metal powder B to obtain the mixed powder.

6. A method for evaluating a structural change in a metal material during a production process, the metal material produced by subjecting a polycrystalline body containing a crystal grain A containing an element X having a plurality of isotopes to grain boundary diffusion, the method comprising:

a first step of adhering a material containing an element X having an isotopic ratio RB different from an isotopic ratio RA of the element X contained in the crystal grain A to a surface of the polycrystalline body, to produce a diffusion precursor;

a second step of cutting a needle-shaped sample from the diffusion precursor, and subjecting the sample to atom probe analysis;

a third step of heat-treating the diffusion precursor to diffuse the element X along a crystal grain boundary;

a fourth step of cutting a needle-shaped sample from the diffusion precursor after a heat treatment, and subjecting the sample to atom probe analysis; and a fifth step of comparing element information obtained by subjecting the diffusion precursor before a heat treatment to atom probe analysis with element information obtained by subjecting the diffusion precursor after a heat treatment to atom probe analysis, and measuring a change in isotopic distribution over time.

* * * * *